(12) United States Patent
Whitefield et al.

(10) Patent No.: US 7,732,450 B2
(45) Date of Patent: Jun. 8, 2010

(54) ANTIFUNGAL KETOCONAZOLE COMPOSITION FOR TOPICAL USE

(75) Inventors: Martin Whitefield, London (GB); Andrew James Dixon, Hitchin (GB); Susan Colette Temple, Hitchin (GB)

(73) Assignee: Boult Wade Tennant, London (GB)

( * ) Notice: Subject to any disclaimer, the term of this patent is extended or adjusted under 35 U.S.C. 154(b) by 940 days.

(21) Appl. No.: 10/343,984

(22) PCT Filed: Aug. 14, 2001

(86) PCT No.: PCT/GB01/03634

§ 371 (c)(1), (2), (4) Date: Feb. 5, 2003

(87) PCT Pub. No.: WO02/15936

PCT Pub. Date: Feb. 28, 2002

(65) Prior Publication Data

US 2004/0063722 A1 Apr. 1, 2004

(30) Foreign Application Priority Data

Aug. 18, 2000 (GB) ................. 0020486.7

(51) Int. Cl.
*A61K 31/496* (2006.01)
*A61K 31/50* (2006.01)
(52) U.S. Cl. ................. 514/254.07; 514/252.1
(58) Field of Classification Search ............ 514/254.07
See application file for complete search history.

(56) References Cited

U.S. PATENT DOCUMENTS 5,100,908 A 3/1992 Murata et al.
5,461,068 A 10/1995 Thaler et al.
5,654,293 A * 8/1997 Francois et al. ............ 514/171
6,046,238 A * 4/2000 Yu et al. .................... 514/553
6,159,479 A * 12/2000 Pinzon ....................... 424/401

OTHER PUBLICATIONS

Search Report, Feb. 8, 2001.
Salicylic Acid [online], 6 pgs. [retrieved from internet on Aug. 8, 2008 using URL <http://en.wikipedia.org/wiki/Salicylic_acid>].
Ketoconazole [online], 6 pgs. [retrieved from internet on Aug. 8, 2008 using URL <http://en.wikipedia.org/wiki/Ketoconazole>].
Ketoconazole (DB01026) [online], 18 pgs. [retrieved from internet on Aug. 8, 2008 using URL <http://www.drugbank.ca/cgi-bin/show_drug.cgi?CARD=APRD00401>].
Data From SRC PhysProp Database for CAS No. 065277-42-1 [online], 1 pg. [retrieved from internet on Aug. 8, 2008 via URL <http://www.drugbank.ca/cgi-bin/show_drug.cgi?CARD=APRD00401> at <http://esc.syrres.com/interkow/webprop.exe?CAS=65277-42-1>].
Ketoconazole MSDS [online], 6 pgs. [retrieved from internet on Aug. 8, 2008 via URL <http://www.drugbank.ca/cgi-bin/show_drug.cgi?CARD=APRD00401> at <http://www.drugbank.ca/public/files/drug_files/msds_sheets/DB01026.pdf>].
XOLEGEL (Ketoconazole, USP) Gel FDA Label, [retrieved from internet on Aug. 8, 2008 via URL <http://www.drugbank.ca/cgi-bin/show_drug.cgi?CARD=APRD00401>at <http://www.drugbank.ca/public/files/drug_files/fda_labels/DB01026.pdf>].

* cited by examiner

*Primary Examiner*—Yong S Chong

(57) ABSTRACT

A pharmaceutical composition suitable for topical application comprising ketoconazole in a solution which comprises: (i) 13 to 50 wt % water; (ii) 45 to 85 wt % of an alcohol having a boiling point of less than 100° C.; and (iii) 2 to 30 wt % of a non-volatile, water miscible, non-ionic surface active agent; the ketoconazole being present in an amount of 0.5 to 3 st % relative to components (i), (ii) and (iii).

12 Claims, No Drawings

ANTIFUNGAL KETOCONAZOLE COMPOSITION FOR TOPICAL USE

CROSS REFERENCE TO RELATED PATENT APPLICATIONS

This application is a national phase application under 35 U.S.C. §371 of International Patent Application No. PCT/GB01/03634, filed Aug. 14, 2001, which claims priority to prior United Kingdom Patent Application No. GB 0020486.7, filed Aug. 18, 2000, both of which are incorporated by referenced herein in their entirety.

FEDERALLY SPONSORED RESEARCH STATEMENT

Not applicable.

REFERENCE TO MICROFICHE APPENDIX

Not applicable.

FIELD OF THE INVENTION

The present invention relates to a pharmaceutical composition for topical application comprising a fungicidally active imidazole derivative, namely ketoconazole.

BACKGROUND OF THE INVENTION

Imidazole derivatives are known which have a wide spectrum of antimicrobial activity both in vitro and in vivo and which can be used topically in the treatment of skin diseases such as dermatophytosis, cutaneous candidosis, onychomycosis, tinea capitis and pityrosporosis. In addition, they can be used topically in the treatment of seborrheic dermatitis, pityriasis capitis and pityriasis versicolor which all involve the yeast *Malassezia furfur*.

One such imidazole derivative, ketoconazole, was originally described in U.S. Pat. No. 4,335,125 in which its principal utility was given as an antifungal compound. Ketoconazole is also disclosed in U.S. Pat. No. 4,569,935 to be useful in the topical treatment of psoriasis and seborrheic dermatitis.

U.S. Pat. No. 4,298,604 describes topical compositions containing the corticosteroid betamethasone dipropionate and, as a fungicidally active agent, clotrimazole.

Ketoconazole, however, has very poor solubility characteristics in common solvents such as water and alcohols. For topical use it is only available commercially at a concentration of 2 wt % in suspension in a semi-solid aqueous cream and in a shampoo for application to the scalp.

Both of these commercial formulations have disadvantages. The cream provides poor bioavailability of ketoconazole as the discrete particles thereof do not permeate very efficiently into the skin. In addition, the cream is not suitable for application to the hair bearing areas of the body, particularly the scalp. The cream is difficult to apply and localise over the affected area and is also cosmetically unacceptable if left on the skin for any length of time as it leaves a greasy deposit.

The shampoo is designed to be left on the scalp for only very short periods which therefore does not provide the extended contact time necessary to maintain a therapeutically adequate concentration on the scalp. It is also difficult to get the active drug to the scalp if the shampoo is not massaged in correctly. Furthermore shampoos tend to contain anionic surfactants which may hinder the drug permeating through the skin and may also irritate the skin.

There is therefore a need for a composition comprising a suitable concentration of ketoconazole for direct application to the skin in order to treat susceptible infective conditions, which can be used on skin bearing hair such as the scalp, and which has cosmetically acceptable characteristics and good permeability through the skin.

Desirably such a product should be a true evaporative solution of low viscosity and once applied it should leave a relatively small liquid residue.

SUMMARY OF THE INVENTION

Embodiments of the invention meet the aforementioned need by one or more of the following aspects. In one aspect, the invention relates to a pharmaceutical composition suitable for topical application comprising ketoconazole in a true solution which comprises: (i) 13 to 50 wt % water; (ii) 45 to 85 wt % of an alcohol having a boiling point of less than 100° C.; and (iii) 2 to 30 wt % of a non-volatile, water miscible, non-ionic surface active agent; wherein the ketoconazole is present in an amount of 1.5 to 2.5 wt % relative to components (i), (ii) and (iii). In some embodiments, the ketoconazole is present in an amount of about 2%; the water is present in an amount of 34 to 36 wt %; the alcohol is present in an amount of 54 to 56 wt %; the surface active agent is present in an amount of 9 to 11 wt %. The alcohol may be isopropyl alcohol. The surface active agent can be polyethoxylated glyceryl cocoate containing 7 ethoxy groups/mole. The composition may further comprise a dermatologically active corticosteroid.

In another aspect, the invention relates to the use of the above composition in the manufacture of a medicament for the treatment of dermatophytosis, cutaneous candidosis, seborrheic dermatitis, tinea capitis, pityriasis capitis, pityriasis versicolor, onychomycosis or pityrosporosis.

In yet another aspect, the invention relates to a pharmaceutical composition suitable for topical application comprising ketoconazole in a true solution. The pharmaceutical composition comprises (i) 34 to 36 wt % water; (ii) 54 to 56 wt % isopropyl alcohol; and (iii) 9 to 11 wt % polyethoxylated glyceryl cocoate; wherein the ketoconazole is present in an amount of 1.5 to 2.5 wt % relative to components (i), (ii) and (iii). In some embodiments, the composition further comprise a dermatologically active corticosteroid.

In still another aspect, the invention relates to the use of the above composition in the manufacture of a medicament for the treatment of dermatophytosis, cutaneous candidosis, seborrheic dermatitis, tinea capitis, pityriasis capitis, pityriasis versicolor, onychomycosis or pityrosporosis.

Additional aspects of the invention and characteristics and properties of the embodiments of the invention become apparent with the following description.

BRIEF DESCRIPTION OF THE DRAWINGS

Not applicable.

DESCRIPTION OF EMBODIMENTS OF THE INVENTION

The present invention therefore seeks to provide a composition having cosmetic acceptability and a solvent medium from which dissolved ketoconazole can continue to permeate into the skin over an extended contact period for maximum thermodynamic activity.

Initial attempts to achieve this composition highlighted significant difficulties due to the solubility capacity of most dermatologically acceptable solvent systems. Even in purely alcoholic solvents, which are known to treat scalp conditions, there was insufficient solubility. For example, the solubilities of ketoconazole, in each of isopropyl alcohol, water and polyethoxylated glyceryl cocoate were found to be 0.4722 wt %, 0.0233 wt % and 0.8682 wt % respectively.

Additional problems occurred with volatile solvents which had a rapid evaporation after application because ketoconazole was deposited onto the skin or scalp in a relatively inactive crystalline form. The addition of water to slow down evaporation did not assist because it provided an even lower solubility capacity and similar crystallisation still occurred.

Quite unexpectedly, however, we have discovered a solvent system comprising three components which provides greater solubility of ketoconazole of up to about 3 wt %, an appropriate evaporation rate and which leaves little or no crystalline residue after evaporation. Although each of the three components mentioned above has little solubilising capacity in its own right for ketoconazole, a mixture of these solvents in a ternary solvent system surprisingly provided an unexpected improved overall solubility.

The present invention accordingly provides a pharmaceutical composition suitable for topical application comprising ketoconazole in a solution which comprises:
(i) 13 to 50 wt % water;
(ii) 45 to 85 wt % of an alcohol having a boiling point of less than 100° C.; and
(iii) 2 to 30 wt % of a non-volatile, water miscible, non-ionic surface active agent;

the ketoconazole being present in an amount of 0.5 to 3 wt % relative to components (i), (ii) and (iii).

In this composition ketoconazole is entirely in true solution, even in cold climatic conditions, in a cosmetically elegant solvent system and can be accurately localised on the skin or scalp without leaving a messy residue. In addition, the activity of the ketoconazole has been shown to be much greater than that provided by the presently available creams and shampoo formulations.

The ketoconazole may be in the free base form.

Ketoconazole is the generic name of 1-acetyl-4-[4-[2-(2, 4-dichlorophenyl)-2-imidazol-1-ylmethyl-1,3-dioxolan-4-ylmethoxy]phenyl]piperazine. The preferred ketoconazole compound is the (±)-(cis) form of the free base form.

The ketoconazole is included in the composition in an amount of 0.5 to 3 wt %, preferably 1.5 to 2.5 wt %, and in particular about 2 wt %, based on the total amount of components (i), (ii) and (iii). At concentrations below 0.5 wt %, the effectiveness begins to diminish to unacceptable levels, and at concentrations higher than about 3 wt %, the limited solubility of the ketoconazole becomes a significant factor.

The alcohol has a boiling point of less than 100° C., preferably less than 85° C. The alcohol assists in dissolving the imidazole derivative and keeping it in a homogeneous solution. Suitable alcohols are ethanol and isopropyl alcohol. Isopropyl alcohol is preferred. The alcohol can be used singly or in a combination of two or more.

The alcohol is included in the solution in an amount of 45 to 85 wt %, preferably 50 to 60 wt %, more preferably 54 to 56 wt % and in particular about 55 wt %.

The non-volatile, water miscible, non-ionic surface active agents used herein are broadly defined as non-ionic surface active compounds with one or more uncharged hydrophilic substituents. A major class of non-ionic surface active agents are those compounds produced by the condensation of alkylene oxide groups with an organic hydrophobic material which may, for example, be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Examples of suitable non-ionic surfactants include polyoxyethylene or polyoxypropylene condensates of aliphatic carboxylic acids or mixtures thereof and mono, di and triglycerides and mixtures thereof, whether linear or branched-chain and unsaturated or saturated, containing from 8 to 18 carbon atoms in the aliphatic chain and incorporating from 2 to 24 ethylene oxide and/or propylene oxide units. Suitable carboxylic acids include coconut fatty acids which contain an average of 12 carbon atoms, tallow fatty acids which contain an average of about 18 carbon atoms, palmitic acid, myristic acid, stearic acid and lauric acid.

Other examples of useful non-ionic surface active agents are polyoxyethylene or polyoxypropylene condensates of aliphatic alcohols containing one, two or three or more hydroxy groups, whether linear or branched chain and unsaturated or saturated, containing from 6 to 24 carbon atoms and incorporating from 2 to 24 ethylene oxide and/or propylene oxide units. Suitable alcohols include coconut fatty alcohol, tallow fatty alcohol, lauryl alcohol, myristyl alcohol and oleyl alcohol.

In a preferred embodiment polyethoxylated glyceryl cocoate is used. This is available commercially as Glycerox HE from Croda Chemicals Limited. In a further preferred embodiment polyethoxylated glyceryl cocoate containing 7 ethoxy groups/mole is used. The surface active agent is included in the solvent in an amount of 2 to 30 wt %, preferably 7 to 20 wt %, more preferably 9 to 11 wt % and in particular about 10 wt %. The surface active agent can be used singly or in a combination of two or more.

Water is included in the solvent in an amount of 13 to 50 wt %, preferably 30 to 40 wt %, more preferably 34 to 36 wt % and in particular about 35 wt %.

Without regard to the defined proportions in the composition, the solution may have to be made shortly before use since its stability and/or solubility may not necessarily be sufficient to allow storage for an extended time. However, we have surprisingly discovered a composition which remains stable and soluble for at least 2 years even at refrigerator temperatures.

Thus the present invention also provides a pharmaceutical composition suitable for topical application comprising ketoconazole in a solution which comprises:
(i) 34 to 36 wt % water;
(ii) 54 to 56 wt % isopropyl alcohol; and
(iii) 9 to 11 wt % polyethoxylated glyceryl cocoate;

the ketoconazole being present in an amount of 0.5 to 3 wt % relative to components (i), (ii) and (iii).

The compositions according to the invention can optionally comprise further components such as a dermatologically active corticosteroid, colouring agent, and pH adjusting agents such as acids or bases or buffers. However, the compositions may consist essentially or consist only of ketoconazole and water, alcohol and surface active agent, optionally together with a corticosteroid, colouring agent and/or pH adjusting agent or buffer.

The corticosteroid can, for example, be present in the usual concentration, e.g. 0.05 to 0.1 wt %. A suitable corticosteroid is betamethasone dipropionate. This can be added to the formulation and allowed to dissolve in the same solvent system. This is particularly suitable when an infection of the skin is accompanied by inflammation.

The pH of the compositions can be adjusted by addition of an acid such as hydrochloric acid or a base such as sodium hydroxide. Acids and/or bases or buffers can be included in the compositions to maintain the pH of the compositions to, for example, from 6 to 8, and most preferably at about 7.5.

The compositions can be prepared by mixing together, in any order, the required components. For example, the surface active agent can be added to the water followed by addition of the alcohol. The ketoconazole is generally added to the solvent system after it has been formed.

The compositions can be used in a method of treatment of the human or animal body by therapy. A suitable method of treatment is to apply to the affected area of skin of a subject in need of such treatment, or liable to be in need of such treatment, an effective amount of the composition of the invention.

The compositions are suitable for application to the skin, scalp, other hair bearing areas of the body and parts of the body where the skin is particularly thick as on the sides or soles of the feet. They can be used topically in the treatment of skin diseases such as dermatophytosis, cutaneous candidosis, seborrheic dermatitis, tinea capitis, pityriasis capitis, pityriasis versicolor, onychomycosis and pityrosporosis.

The present invention also provides a use for the compositions in the manufacture of a medicament for the treatment of dermatophytosis, cutaneous candidosis, seborrheic dermatitis, tinea capitis, pityriasis capitis, pityriasis versicolor, onychomycosis or pityrosporosis.

The compositions may be applied topically to the affected area and immediately surrounding area of the skin or scalp with an amount sufficient to coat the areas with a thin film. In a preferred embodiment this amount is from 0.5 to 2 ml per application.

Desirably the composition should be applied to the affected area twice daily, preferably morning and night, over a period of from two to three weeks. It is evident, however, that the dosage schedule may be altered depending on the response of the treated subject and/or depending on the evaluation of the physician prescribing the compositions of the instant invention.

The composition can be packaged in a suitable container such as a bottle. Preferably the composition is applied to the desired area through an extended fine nozzle when the composition is to be applied to the scalp through hair.

The following Examples further illustrate the present invention.

EXAMPLE 1

A batch of a pharmaceutical composition was prepared.

285 kg of purified water EP/BP, 1 kg of Hexaplate Sunset Yellow 9600 solution (0.1% w/v), 10 kg of Glycerox HE and 55 kg of isopropyl alcohol were added to a mixing vessel.

2 kg of ketoconazole in powder form was added to the mixing vessel, which was then sealed and the mixture stirred until the ketoconazole had dissolved. Subsequently the pH of the mixture in the vessel was adjusted to 7.5 by the addition of 1M sodium hydroxide solution.

A small additional amount of purified water EP/BP was then added to the mixing vessel. This amount depends on the amount of sodium hydroxide solution which has been added.

The balance outstanding from the quantities used is 500 g. Therefore, the calculation used to calculate the amount of water required is:

$$\text{Amount (in } g \text{) of additional purified water required} = 500 - 1 \, M \text{ sodium hydroxide solution required.}$$

In this Example 224.79 grams of sodium hydroxide solution was added. Therefore 275.21 g of additional purified water was required.

Finally 100 ml bottles were each filled with 91.6 g of the mixture.

EXAMPLE 2

This Example compares the skin permeation rate and distribution of ketoconazole over a 24 hour period using human tissue in vitro of two commercially available formulations, namely a scalp application in the form of a cream (A) and a shampoo (B), and the ketoconazole formulation of the present invention prepared as in Example 1 (C).

The guidelines suggested by the FDA and AAPS were followed (Skelly et al, Pharmaceutical Research, 1987, 4, 265-267).

Epidermal membranes, comprising both stratum corneum and epidermis, were prepared from cosmetic reduction skin by blunt dissection and subsequent heat separation at 60° C. for 50 seconds.

The epidermal membranes were then floated onto filter paper supports and mounted as a barrier between the halves of diffusion cells with the stratum corneum facing a donor chamber. Twelve replicates were run for each formulation. Four replicate control cells were also run. The receptor chambers were filled with 25% ethanol in a phosphate buffered saline (pH 7.4), capped and allowed to equilibrate to the correct temperature. The skin surface temperature was maintained at 32±1° C. The formulations were applied to the skin surface at a dose of 5 mg/cm$^2$.

After 24 hours the diffusion cells were dismantled and each skin sample was placed onto a drop of cyanoacrylate glue on a plastic card. The skin surfaces were then wiped with a cotton bud which was then extracted with an HPLC mobile phase and analysed for ketoconazole content. Each skin sample was then tape stripped ten times with D-Squame tape by a single operator. The tape strips for each cell were grouped and placed in the same vial as follows:

| | |
|---|---|
| Group 1 | Strip 1 |
| Group 2 | Strips 2-10 |

The ketoconazole was extracted from the taped strips by the addition of an HPLC mobile phase and vortexing at high speed for 2 minutes. 200 µl of each sample was then placed into an autosampler vial and analysed for ketoconazole content.

The remaining samples of skin were extracted into an HPLC mobile phase and the extracts analysed for ketoconazole content.

The amount of ketoconazole present in the stratum corneum was deduced from the amount of ketoconazole present in strips 2 to 10.

The amount of ketoconazole present in the whole skin was deduced from the sum of the amount of ketoconazole present in strips 2 to 10 and the remaining skin.

Strip 1 was excluded as this did not measurably reflect the extent of diffusion and only contained the product, if any, which was not removed in the wiping-off process.

Penetration of Ketoconazole Through Human Skin (In-Vitro) from Three Formulations (24 Hours Contact)

Mean of 12 replicates
A. NIZORAL™ CREAM (2% Ketoconazole PL 0242/0107)
  Amount present in the stratum corneum: 0.45 μg/cm$^2$
  Amount present in the whole skin: 1.95 μg/cm$^2$
B. NIZORAL™ SHAMPOO (2% Ketoconazole PL 0242/0139)
  Amount present in the stratum corneum: nil
  Amount present in the whole skin: nil
C. Ketoconazole Scalp Application
  Amount present in the stratum corneum: 1.60 μg/cm$^2$
  Amount present in the whole skin: 7.13 μg/cm$^2$

EXAMPLE 3

The solubility of ketoconazole in each of isopropyl alcohol, water and polyethoxylated glyceryl cocoate were established at room temperature (21° C.).

| Solvent Medium | Solubility |
|---|---|
| Isopropyl alcohol | 0.4722 wt % |
| Water | 0.0233 wt % |
| Polyethoxylated glyceryl cocoate | 0.8682 wt % |

The solubility of ketoconazole in a composition of the present invention, prepared as in Example 1, containing 55% isopropyl alcohol, 35% water and 10% polyethoxylated glyceryl cocoate was also established at room temperature (21° C.).

The solubility of ketoconazole was found to be 2.8 wt %.

This demonstrates the significant increase in solubility provided by the composition of the present invention.

EXAMPLE 4

Samples were prepared using the method outlined in Example 1, containing the 2% ketoconazole in a composition containing 55% isopropyl alcohol, 35% water and 10% polyethoxylated glycerol cocoate. These were then stored in a refrigerator at 4° C. to determine whether crystallization occurred.

After a period of four weeks at this temperature no crystals of ketoconazole appeared. This confirmed that the composition could form the basis of a commercial product which would remain as a clear solution even if stored throughout cold winter conditions.

A further three batches of this composition were then stored over a period of 6 months at elevated temperatures of 25° C., 30° C. and 40° C. No detectable deterioration of the ketoconazole was observed.

What is claimed is:

1. A pharmaceutical composition suitable for topical application comprising:
  a true solution comprising:
  (i) 13 to 50 wt % water;
  (ii) 45 to 85 wt % of an alcohol having a boiling point of less than 100° C.; and
  (iii) 2 to 30 wt % of a non-volatile, water miscible, non-ionic surface active agent; and
  (iv) ketoconazole, the ketoconazole being present in an amount of 1.5 to 2.5 wt % relative to components (i), (ii) and (iii).

2. A composition according to claim 1 wherein said ketoconazole is present in an amount of about 2%.

3. A composition according to claim 1 wherein said water is present in an amount of 34 to 36 wt %.

4. A composition according to claim 1 wherein said alcohol is present in an amount of 54 to 56 wt %.

5. A composition according to claim 1 wherein said surface active agent is present in an amount of 9 to 11 wt %.

6. A composition according to claim 1 wherein said alcohol is isopropyl alcohol.

7. A composition according to claim 1 wherein said surface active agent is polyethoxylated glyceryl cocoate containing 7 ethoxy groups/mole.

8. A composition according to claim 1 which also comprises a dermatologically active corticosteroid.

9. A pharmaceutical composition suitable for topical application comprising:
  a true solution comprising:
  (i) 34 to 36 wt % water;
  (ii) 54 to 56 wt % isopropyl alcohol; and
  (iii) 9 to 11 wt % polyethoxylated glyceryl cocoate; and
  (iv) ketoconazole, the ketoconazole being present in an amount of 1.5 to 2.5 wt % relative to components (i), (ii) and (iii).

10. A composition according to claim 9 which also comprises a dermatologically active corticosteroid.

11. A method for making a pharmaceutical composition for the topical treatment of dermatophytosis, cutaneous candidosis, seborrheic dermatitis, tinea capitis, pityriasis capitis, pityriasis versicolor, onychomycosis or pityrosporosis comprising:
  forming a true solution comprising:
  (i) 13 to 50 wt % water;
  (ii) 45 to 85 wt % of an alcohol having a boiling point of less than 100° C.; and
  (iii) 2 to 30 wt % of a non-volatile, water miscible, non-ionic surface active agent; and
  (iv) ketoconazole, the ketoconazole being present in an amount of 1.5 to 2.5 wt % relative to components (i), (ii) and (iii).

12. A method for making a pharmaceutical composition for the topical treatment of dermatophytosis, cutaneous candidosis, seborrheic dermatitis, tinea capitis, pityriasis capitis, pityriasis versicolor, onychomycosis or pityrosporosis comprising:
  forming a true solution comprising:
  (i) 34 to 36 wt % water;
  (ii) 54 to 56 wt % isopropyl alcohol; and
  (iii) 9 to 11 wt % polyethoxylated glyceryl cocoate; and
  (iv) ketoconazole, the ketoconazole being present in an amount of 1.5 to 2.5 wt % relative to components (i), (ii) and (iii).

* * * * *

UNITED STATES PATENT AND TRADEMARK OFFICE
CERTIFICATE OF CORRECTION

| | | |
|---|---|---|
| PATENT NO. | : 7,732,450 B2 | Page 1 of 1 |
| APPLICATION NO. | : 10/343984 | |
| DATED | : June 8, 2010 | |
| INVENTOR(S) | : Whitefield et al. | |

It is certified that error appears in the above-identified patent and that said Letters Patent is hereby corrected as shown below:

Title page, item [73] should read as follows:
Assignee: Diomed Developments Limited Signed and Sealed this
Twenty-fourth Day of May, 2011

David J. Kappos
*Director of the United States Patent and Trademark Office*